United States Patent [19]

Long, Jr.

[11] Patent Number: 5,393,513
[45] Date of Patent: Feb. 28, 1995

[54] STABLE, HIGHLY CONCENTRATED FLUORO CARBON EMULSIONS

[75] Inventor: David M. Long, Jr., El Cajon, Calif.

[73] Assignee: Alliance Pharmaceutical Corp., San Diego, Calif.

[21] Appl. No.: 100,664

[22] Filed: Jul. 30, 1993

Related U.S. Application Data

[63] Continuation of Ser. No. 811,026, Dec. 19, 1991, abandoned, which is a continuation of Ser. No. 387,947, Aug. 24, 1989, Pat. No. 5,080,885, which is a continuation of Ser. No. 818,690, Jan. 14, 1986, Pat. No. 4,865,836.

[51] Int. Cl.$^6$ .............. A61K 49/04; A61K 31/56; A61K 31/35; A61B 5/055
[52] U.S. Cl. .................................. 424/5; 424/9; 128/653.4; 436/173; 514/169; 514/171; 514/460; 514/744; 514/757; 514/832; 514/937; 514/941; 514/943
[58] Field of Search .............. 424/5, 9; 128/653.4, 128/654; 436/173; 514/169, 171, 460, 744, 757, 937, 832, 941, 943

[56] References Cited

U.S. PATENT DOCUMENTS

| | | | |
|---|---|---|---|
| 3,818,229 | 6/1974 | Long, Jr. | 250/312 |
| 3,958,014 | 5/1976 | Watabe et al. | 424/366 |
| 3,975,512 | 8/1976 | Long | 424/5 |
| 4,073,879 | 2/1978 | Long, Jr. | 424/5 |
| 4,105,798 | 8/1979 | Moore et al. | 424/352 |
| 4,146,499 | 3/1979 | Rosano | 252/186 |
| 4,397,870 | 8/1983 | Sloviter | 424/325 |
| 4,450,481 | 5/1984 | Osterholm | 604/24 |
| 4,917,930 | 3/1990 | McCormick | 424/78 |

FOREIGN PATENT DOCUMENTS 0231091 7/1984 European Pat. Off.

OTHER PUBLICATIONS

Beisbarth, H. and T. Suyama, 5th Intl. Symp. on Perfluorochemical Blood Substitutes. Mainz: Mar. 1981.
Persico, D. et al., A General Systhesis for Symmetrical Highly Branched Perfluoro Ethers J. Org. Chem. 50:5156–5169 (1985).
Sharts, C. and H. Reese, The Solubility of Oxygen in Aqueous Flurocarbon Emulsions. J. Fluorine Chemistry 11:637–641 (1978).
S. Davis, 2nd International Symposium on Clinical Nutrition Advances in Clinical Nutrition 19:213–239, Bermuda: May 1982.
Yokoyama, K. et al., Preparatiion of Perfluorodecalin Emulsion, and Approach to the Red Cells Substitute, Fed. Proc. 34(6) 1478–1483 (1975).
Steiner, M. and J. Anastasi, J. Clinical Investigation 57:732–737 (1976).
Pandolfe, W. D. and R. R. Kinney, "Recent Developments in the Understanding of Homogenization Parameters" Denver, Colo. Aug. 29, 1983.
Chandonnet, S. et al., Preparation of Microemulsions by Microfluidization, Feb. 1985.
Korstvedt, H. et al., Microfluidization: for Making Fine Emulsions and Dispersions, Amer. Paint and Coatings Journal, Jan. 28, 1985.

(List continued on next page.)

*Primary Examiner*—Gary E. Hollinden
*Attorney, Agent, or Firm*—Knobbe, Martens, Olson & Bear

[57] ABSTRACT

A non-toxic, brominated perfluorocarbon emulsion for internal and intravenous use in animals (including humans) is disclosed, for use as an oxygen transport medium and as a contrast enhancement medium capable of facilitating the detection of tumors and other elements within the body. This emulsion is stable and maintains its very small particle size characteristics for extended periods of time, often exceeding eighteen months after sterilization, and further may include a stabilizing component selected from the group consisting of steroids, tocopherols, cholesterols, and combinations thereof. An anti-oxidizing component enhances delivery in oxygen transport.

14 Claims, No Drawings

OTHER PUBLICATIONS

Korstvedt, H. et al., Microfluidization, Drug and Cosmetic Industry, Nov. 1984.

Allinger, H., Ultrasonic Disruption, American Laboratory, Oct. 1985.

Berlinger, S. Application of Ultasonic Processors, Biotechnology Laboratory, Mar. 1984.

Gould, S. et al., Assessment of a 35% Fluorocarbon Emulsion, The Journal of Trauma 23(8):720–724 1983.

Police, A. M. et al., Critical Care Medicine 13(2):96–98 1985.

Nunn, G. R. et al., Effect of Fluorocarbon Exchange Tranfusion on Myocardial Infarction Size in Dogs, American J. of Cardiology 52:203–205 1983.

Bose, B. et al., Brain Research 328:223–231 1985.

Spears, J. et al., Circulation (Abstracts) 68 (Supp. III) No. 317 Oct. 1983.

Patel, M. et al., Survival and Histopathological Changes in Lungs of Hamsters following Liquid Synthetic Breathing Fed. Proceedings 29(5):1740–1745 1970.

A Technical Bulletin #67 of the Fauling Corporation Sep. 1982 Peck, W. W. et al., Investigative Radiology 19:129 1984.

Gaulin Corp. A Technical Bulletin #67, Sep. 1982.

Dobben, G. et al., Experimenta Studies with Radiopaque Fluorocarbon in the Subarchnoid Space, Neuroradiology 6:17–19 1973.

Brahme, F. et al., Investigative Radiology 11(4):319–330 1976.

Long, D. M. et al., Radiology 105(2):323–332 1972.

Riess, Jean, Artificial Organs 8:34–56 1984.

STABLE, HIGHLY CONCENTRATED FLUORO CARBON EMULSIONS

CROSS-REFERENCE TO RELATED APPLICATION

This application is a continuation of application Ser. No. 07/811,026, filed Dec. 19, 1991, now abandoned, which is a continuation of application Ser. No. 07/387,947, filed Aug. 24, 1989, now U.S. Pat. No. 5,080,885, which is a continuation of application Ser. No. 06/818,690, filed Jan. 14, 1986, now U.S. Pat. No. 4,865,836.

BACKGROUND OF THE INVENTION

1. Field of the Invention

The present invention relates to the art of non-toxic oxygen transport and contrast enhancement agents, and more particularly, to stable emulsions capable of sterilization and suitable for internal and intravenous animal (including human) use, where the emulsion is a brominated perfluorocarbon in the discontinuous phase in the presence of certain substances which are believed to be stabilizing agents.

2. Description of the Prior Art

Mono-brominated cyclic and acyclic perfluorocarbons in aqueous emulsions with a minor amount of an emulsifying agent have been known for medical applications involving animals, including humans, for both radiopacity and oxygen delivery. Oxygen is highly soluble in, for example, perfluorooctylbromides. (See, Long, U.S. Pat. No. 3,818,229; No. 3,975,512; and No. 4,073,879.) The present invention is directed toward improvements in the use of such bromofluorocarbons wherein the oxygen transport characteristics, as well as the storage characteristics of the emulsions are enhanced, while the toxicity is further minimized or decreased altogether.

In the past, efforts to use emulsified fluorocarbons as an oxygen transport or carrier, as in a blood substitute, have encountered certain difficulties. Purity, non-toxicity, chemical and biological inertness and excretability are necessary objectives. The emulsified fluorocarbon must be capable of sterilization, preferably by heat, have long-term size and function stability in the fluid or non-frozen state, be industrially feasible, persist for sufficiently long times in the bloodstream when used intravascularly and be eliminated rapidly from the body. It has been conventionally believed that those fluorocarbons which have fast elimination times from the body do not form stable emulsions, and that those fluorocarbons which form stable emulsions are retained too long in the body. Non-brominated perfluorocarbons show a direct relationship between emulsion stability and molecular weight and an inverse relationship between molecular weight and excretion rates from the animal body. Both types of fluorocarbons are inadequate, and attempts to combine amounts of both types have merely combined the problems of each.

For intravenous use, it is considered important to have small particle size. However, long-term storage for extended periods of time for a month and longer, of fluorocarbon blood substitutes, or "synthetic blood" has hereto for resulted in conglomeration of the fluorocarbon particles of the emulsion into large particles, specially after heat sterilization. For a general discussion of the objectives and a review of the efforts and problems in achieving these objectives in fluorocarbon blood substitutes, see "Reassessment of Criteria for the Selection of Perfluoro Chemicals for Second-Generation Blood Substitutes: Analysis of Structure/Property Relationship" by Jean G. Riess, *Artificial Organs* 8, 34–56 (1984).

Larger particle sizes are dangerous in intravenous use in that they tend to collect in the lung, spleen and some other organs, enlarging them and endangering their functioning. On the other hand, it is desired to have sufficient particle size in the fluorocarbon particles for them to collect in tumors and other areas when the fluorocarbons are used as a contrast enhancement medium. Larger particle sizes, also are unobjectionable when used in other, non-venous systems in the body, such as, for example, the cerebrospinal fluid ventricles and cavities.

DESCRIPTION OF THE PREFERRED EMBODIMENTS

In brief, one aspect of the present invention comprises mono-brominated perfluorocarbon emulsions. The bromofluorocarbon emulsions found suitable for use as an oxygen transport medium comprise mono-brominated perfluorocarbons having a minor Mount of an emulsifying agent and further comprising a compound believed to be useful in stabilizing the membrane of the bromofluorocarbon particle. The compound could be steroid hormones, cholesterol, tocopherols and mixtures thereof. A nine-alpha fluorinated corticosteroid in combination with cholesterol emulsified along with a phosphatidylcholine to particles of a perfluorooctylbromide having the formula $CF_3(CF_2)_6CF_2Br$ or $C_8F_{17}Br$, or of related brominated perfluorocarbon such as a perfluorohexylbromide ($C_6F_{13}Br$) or a perfluoroseptobromide ($C_7F_{15}Br$), together with a tocopherol as an anti-oxidant, is preferred.

It has been found that particle size stability can be maintained with emulsions of from 20% weight per volume to 125% weight per volume of the bromofluorocarbon without undesirable viscosity. Herein in this specification, the expression "weight per volume" or "w/v" will be used and understood to mean the ratio of percentage weight per grams per 100 cubic centimeters or milliliters, or equivalent expressions or mathematical identities thereof. Emulsions with concentrations of from 20% to 100% weight per volume have a thixotropic viscosity profile less than that of whole human blood. Perfluorooctylbromide is excreted rapidly from the animal body, because of the lipotrophic nature of the brominated perfluorocarbon, it is believed. In any event and notwithstanding its high molecular weight and stability, mono-brominated perfluorocarbon has a relatively high excretion rate from the animal body.

In some applications where high bromide concentration, such as when the emulsion is to be used as a contrast enhancement medium, or where a high oxygen transport is needed in an intravascular system where large volume impact is to minimized, the larger concentration emulsion is preferred. While it is not certain, it is considered that these suitable and stable high bromofluorocarbon concentration emulsions are possible because of (1) the relatively high molecular weight of the brominated perfluorocarbon, and (2) the good bonding between the bromine and the phospholipid emulsifying agent discussed below.

The preferred emulsifying agent is a phospholipid, an anionic surfactant or a fluorinated surfactant. Suitable phospholipids include lecithin, such as phosphatidylcholine. Phospholipids are common and biologically accepted elements in the blood, and are not so readily phagocytosed by macrophages or other organisms in the animal body's fluids. The resultant emulsion thus is resistent to macrophage and other animal body organism attack.

Preferred anionic surfactants include polyoxyethylenepolyoxypropylene copolymers, such as Plutonit. Suitable fluorinated surfactants include XMO10 and XMO20.

The phospholipid emulsifying agent should be included in the range of from 2 to 14 grams weight per volume, with the preferred amount being 6 grams weight per volume for concentrations of 75% w/v bromofluorocarbon and 7 grams to 10 grams weight per volume for concentrations of 100% bromofluorocarbon. The phospholipid lecithin contains both hydrophilic and hydrophobic or lipophilic characteristics and is thus a suitable emulsifying agent for the perfluorocarbon particle.

According to one embodiment of the present invention, an additional compound is made part of the particle and emulsion. The additional component is believed to be effectual in making the discontinuous particle membrane more compatible and stronger with respect to the continuous, aqueous phase of the emulsion. The additional component could be a tocopherol, asteroid hormone, a cholesterol or, preferably, a combination of these three components. Suitable steroid hormones include fluorinated corticosteroids, fluorinated androgens and non-fluorinated hormones, such as progesterones and estrogens. The preferred steroid is one that is fluorinated in either the 9-alpha or the 6-alpha positions such as, for examples, 9-alpha-fluoro-16-alpha-methylprednisolone, 9-alpha-fluoro-16-betamethylprednisolone, 9-alpha-fluoro-16-alpha-hydroxyprednisolone and 6-alpha-fluoro-16-alpha-methylprednisolone, or combinations of these corticosteroids.

While the actual reaction or membrane structure that takes place is not known, it is believed that the affinity of the fluorine in the fluorinated corticosteroid with the fluorine in the bromofluorocarbon creates a more compatible and reliable bond between the steroid and perfluorocarbon particle to form a more stable membrane for the perfluorocarbon particle in the discontinuous phase of the emulsion.

Red blood cells have cholesterol on their cell membranes removed to be joined with the membrane of the fluorocarbon particles, which form close union with and have an affinity for the fluorocarbon particles, it is believed. Fluorocarbon particles having a significant coating of the cholesterols will deter the removal of cholesterol from the red blood cells, it is believed. Somewhat similarly, tocopherols and steroid hormones enhance the stability of the membrane of the perfluorocarbon particle.

The steroids 9-alpha-fluoro-16-alpha-methylprednisolone and 9-alpha-fluoro-16-beta-methylprednisolones, and other additional components if any are combined with them, should be included in an amount from 0.5 mg. to 5 mg. (or 0.0001 to 0.005 percent) weight per volume (w/v) in the emulsion. Six times this quantity of the steroid 9-alpha-fluoro-16-alpha-hydroxyprednisolone and combined additional components may be used. Three times the range given may be used if the steroid 6-alpha-fluoro-16-alpha-methylprednisolone and any additional component is used. The actual amount of the additional component or components is a function of the contemplated dose, and of the amount of bromofluorocarbon in the ultimate emulsion. In this specification, the term "biocompatible" is used to denote that amount or quantity which is compatible with, and above which toxicity results in, the biological system into which the emulsion containing the biocompatible element is to be introduced. There are biocompatible limits for steroids and cholesterols. It may be that additional amounts or quantities of the steroids and cholesterols are biocompatible, but the range given has been found to be sufficient to achieve the particle size stability and efficacious compatibility with red blood cells and other components in the bloodstream and other fluid systems of the animal body.

Other nutrients may be added to the ultimate emulsion, such as, for example, glucose, amino acids, proteins and lipids.

Oxygen is highly soluble in the perfluorocarbons and in particular the mono-brominated perfluorocarbons of the present invention. In using the present invention as an oxygen transport medium, it is important to retain the oxygen as part of the perfluorcarbon particle for a reasonable period of time in order to transport the oxygen throughout the vascular system or to increase intravascular dwell time. It is found that tocopherols such as alpha-tocopherol and water-soluble analogs of tocopherols are suitable anti-oxidants which will retard rapid oxidation. Other anti-oxidants that are useful are ascorbic acid and calcium ascorbate. Adding anti-oxidants to the emulsion in an amount of from 0.01% to 0.5% weight per volume has been found useful to retard oxidation of the lipid emulsifier which diminishes the stability of the emulsion. Anti-oxidants also quench free radicals such as superoxide or hydroxyl atoms which are harmful to biological systems.

For contrast enhancement use and for oxygen transport use internally in an animal, including humans in other than the bloodstream, such as in the cerebrospinal system, in the eye and in the tracheobronchial passages, for example, larger particle sizes can be tolerated, and indeed may even be preferred. Such larger particle sizes may provide for a more even distribution of the gas, such as oxygen. Particle sizes of less than 400 nanometers diameter for the substantial portion, on the order of 95% of the particles, with a median particle diameter of less than 150 nanometers is to be preferred, however, for use in the bloodstream. Effective oxygen unloading or de-oxygenation occurs in the bloodstream primarily in the capillaries, and the small bromofluorocarbon particle size is advantageous in getting the oxygen to these capillaries. For these sizes for use in the bloodstream, and even for the emulsions to be used in non-vascular systems, it is highly important to maintain particle size characteristics stable over extended periods of time, at least more than one month and of the order of eighteen months and more.

Perfluorocarbon emulsions in commercially usable quantities having very small particle sizes or diameters on the order of hundreds of nanometers using conventional particle fractionalization methods, have been achieved according to methods disclosed herein, such as use of homogenization techniques utilizing the Gaulin mixer. Bromoperfluorocarbon emulsions made with such a technique appear to be suitably stable where the concentration of the bromoperfluorocarbon is relatively small, on the order of less than 50% weight per volume. Attempts using the Gaulin mixer to prepare commercially usable quantities of bromoperfluorocarbon emulsions having w/v concentrations of 50%, 75% and more and having a median particle diameter size of less than 200 nanometers were unsuccessful. These higher concentration bromo-perfluorocarbon emulsions were observed to have a median particle diameter size of more than 200 nanometers.

Long-term, extended period of time small particle size stability of higher concentrations of monobrominated perfluorocarbon emulsion in an aqueous phase with a phospholipid emulsifying agent has been found when the emulsion is formed or generated using a plural flow impingement apparatus. The aqueous phase was buffered with sodium monophosphate and sodium diphosphate in such an amount to give a resultant emulsion pH of between 6.8 and 7.2. The aqueous phase, further, was in a solution of glycerol to control the osmolarity of the resultant emulsion for use in the bloodstream. This buffered, aqueous phase solution in glycerol is sometimes designated the vehicle.

The bromofluorocarbon was metered in a predetermined, measured rate into the vehicle or aqueous phase having the emulsifying agent mixed therein. The resulting mixture was placed into a flow path which was divided into a plurality of flow paths. The flows were re-directed to impinge upon each other at velocities in excess of 1500 feet per second in sheets of interaction in a cavity under 4,000 pounds per square inch or more of pressure. The resulting bromofluorocarbon particles had a size characteristic of more than 95% smaller than 350 nanometers in diameter, with the median size diameter of less than 150 nanometers and, significantly, these size characteristics were maintained stable for up to sixteen months, and even after sterilization, such as by heat or by filtration.

The present invention can be further understood by reference to the following illustrative examples.

EXAMPLE I

Exchange transfusions were performed in female rats weighing 180 to 220 grams. The rats were anesthetized and polyethylene catheters were inserted into the left or right jugular vein and carotid artery. After recovery from the anesthesia, the rats were placed into an atmosphere enriched with 50% to 60% oxygen. Blood was removed through the carotid artery catheter and a comparable amount of the brominated perfluorocarbon emulsion comprising 25% w/v of perfluorooctylbromide, 4% w/v of lecithin, 0.04% w/v of L-alpha-tocopherol, 2.21% w/v of glycerol, 0,012% w/v of sodium diphosphate, 0.057% w/v of sodium monophosphate, and the aqueous phase. The transfusion was continued until the red blood cell count of the rat was reduced to 50% of the baseline value. The rats were kept in the oxygen enriched atmosphere for twenty-four hours, after which they were removed to the ordinary atmosphere. All rats survived for more than one month.

EXAMPLE II

The experiment of Example I was repeated, except that the brominated perfluorocarbon emulsion comprised 50% w/v of perfluorooctylbromide. All other parameters were the same. All rats survived for more than one month.

EXAMPLE III

BALB/c Mice were administered intravenously the brominated perfluorocarbon emulsion at doses of 45 grams per kilogram of body weight, and were administered intraperitoneally the brominated perfluorocarbon emulsion in doses of 100 grams per kilogram of body weight. The emulsion comprised 100% w/v of perfluorooctylbromide, 9.1% w/v of lecithin, 0.2% w/v of 6-alpha-fluoro-16-alpha-methylprednisolone, 0.2% w/v of alpha-tocopherol, 1.0% w/v of glycerol, 0,012% w/v of sodium diphosphate, 0.057% w/v of sodium monophosphate, and the aqueous phase. After seven days the liver and spleen were enlarged, but the peritoneal cavity showed no signs of inflammation, and the lungs were normal and filled with oxygen. There were no signs of hemorrhage or pulmonary congestion, or of inflammation of the tissues of the abdominal wall.

EXAMPLE IV

A mono-brominated perfluorocarbon emulsion comprising 100% w/v of perfluorooctylbromide, 9.1% w/v of lecithin, 0.02% w/v of 6-alpha-fluoro-16-alpha-methylprednisolone, 0.2% w/v of alpha-tocopherol, 1.0% w/v of glycerol, 0.012% w/v of sodium diphosphate, 0.057% w/v of sodium monophosphate, and the aqueous phase, was prepared by first preparing the vehicle of the continuous or aqueous phase by blending in the lecithin, the 6-alpha-fluoro-16-alpha-methylprednisolone, the alpha-tocopherol, the glycerol, the sodium diphosphate, and the sodium monophosphate. The perfluorooctylbromide was added in a measured rate into the vehicle while mixing. The resulting emulsion at 10° C. was passed through a microfluidizing apparatus in the method described herein where a plurality of flows of the emulsion were impinged upon each other at velocities in excess of 1500 feet per second, for 15 passes.

The particle size distribution was analyzed in a Nicomp sub-micron particle sizer manufactured by Pacific Scientific Company of Anaheim, Calif. This analyzer determines relative quantities of various sized particles by a method of dynamic light scattering. Results indicated that the majority of particles ranged in diameter from about 84.2 to 87.2 nanometers, and a significantly smaller population of particles had a diameter ranging from about 200.0 to 252.6 nanometers.

The emulsion was then sterilized at 90° C. for fifteen minutes. After sterilization, the Nicomp emulsion particle sizer characteristics were measured on the Nicomp particle sizer. The results of this analysis showed no significant particle size characteristic deterioration or change from that noted above; the majority of particles again ranged in diameter from about 84.2 to 87.2 nanometers, and a significantly smaller population of particles had a diameter ranging from about 208.6 to 266.6 nanometers.

EXAMPLE V

The emulsion particle size stability over an extended period of time was studied by analyzing the particle size distribution in a Nicomp sub-micron particle sizer identified above in Example IV. The brominated perfluorocarbon emulsion first was made by the methods described above and comprised 25% w/v of perfluorooctylbromide, 4% w/v of lecithin, 0.04% w/v of L-alpha-tocopherol, 2.21% w/v of glycerol, 0.012% w/v of sodium diphosphate, 0.057% w/v of sodium monophosphate, and the aqueous phase. The emulsion was analyzed shortly after formulation, and the relative quantities of the emulsion's particle sizes is as follows: results indicated that the majority of particles ranged in diameter from about 76.5 to 85.7 nanometers, and a significantly smaller population of particles had a diameter ranging from about 240.0 to 359.9 nanometers.

The emulsion was stored at 4° C., although, due to various interruptions during the time of storage, the temperature was changed, and was frequently much higher than 4° C. A second and substantially identical analysis was made using the Nicomp particle sizer as described above, some fifteen months and twenty-two days after the analysis given immediately above. The results of the second analysis indicated that the majority of particles ranged in diameter from about 24.0 to 26.6 nanometers, and two extremely minor populations of particles having a diameter ranging from about 85.7 to 133.3 nanometers and about 200.0 to 1200.0 nanometers were also detected.

The foregoing detailed description of the invention and of the preferred embodiments, as to products, compositions and processes, is illustrative of specific embodiments only. It is to be understood, however, that additional embodiments may be perceived by those skilled in the art. The embodiments described herein, together with said additional embodiments, are considered to be within the scope of the present invention.

I claim:

1. A fluorocarbon emulsion, prepared by:
   forming a mixture consisting essentially of an aqueous phase, an effective amount of emulsifying agent, and a fluorocarbon, said mixture having from greater than 50% to about 125% weight per volume of said fluorocarbon; and
   passing the fluorocarbon-containing mixture through a mechanical emulsification apparatus in which said mixture is subjected to sufficiently high flow rams and pressures to form a stable, heat sterilizable fluorocarbon-in-water emulsion;
   wherein said emulsion is biocompatible and exhibits substantial/particle size stability in the non-frozen state following heat sterilization.

2. The fluorocarbon emulsion of claim 1 wherein the fluorocarbon is a brominated fluorocarbon.

3. The fluorocarbon emulsion of claim 1 wherein the fluorocarbon is a monobrominated perfluorocarbon.

4. The fluorocarbon emulsion of claim 1 wherein the fluorocarbon emulsion has at least 55% weight per volume of fluorocarbon.

5. The fluorocarbon emulsion of claim 1 wherein the fluorocarbon emulsion has at least 60% weight per volume of fluorocarbon.

6. The fluorocarbon emulsion of claim 1 wherein the fluorocarbon emulsion has greater than 75% weight per volume of fluorocarbon.

7. A storage stable, heat sterilizable fluorocarbon emulsion consisting essentially of:
   an continuous aqueous phase, a discontinuous fluorocarbon phase, and an effective mount of emulsifying agent, wherein the concentration of said fluorocarbon phase in said emulsion is greater than 85% and no more than 125%, weight per volume, and wherein said emulsion exhibits substantial particle size stability on storage in the non-frozen state following heat sterilization and is biocompatible.

8. The fluorocarbon emulsion of claim 7 wherein the fluorocarbon is a monobrominated perfluorocarbon.

9. The fluorocarbon emulsion of claim 7 wherein the fluorocarbon is a perfluorooctylbromide.

10. A process for preparing a fluorocarbon emulsion capable of carrying oxygen to animal tissues, said emulsion having substantial particle size stability characteristics for an extended period of time and through heat sterilization, comprising the steps of:
   a. forming a mixture consisting essentially of an effective mount of an emulsifier, an aqueous phase, and from about 55% to 125% weight per volume of a non-toxic fluorocarbon; and
   b. passing the fluorocarbon-containing mixture through a mechanical emulsifying apparatus having a flow path, in which said mixture is subjected to sufficiently high shear rates to form a stable, heat sterilizable emulsion.

11. A process for preparing a fluorocarbon emulsion capable of carrying oxygen to animal tissues, said emulsion having substantial particle size stability characteristics for an extended period of time through heat sterilization comprising the steps of:
   forming a mixture consisting essentially of an aqueous phase with an effective amount of an emulsifier and from about 50% to about 125% weight per volume of a fluorocarbon; and
   passing the fluorocarbon-containing mixture through a mechanical emulsification apparatus in which said mixture is subjected to sufficiently high flow rams and pressures to form a stable, heat sterilizable emulsion.

12. The process of claim 11 wherein said fluorocarbon is brominated.

13. The process of claim 11, wherein said fluorocarbon emulsion has at least 60% weight per volume of fluorocarbon.

14. An emulsion according to claim 3 or claim 7 wherein the emulsifying agent is a phospholipid.

* * * * *

UNITED STATES PATENT AND TRADEMARK OFFICE
CERTIFICATE OF CORRECTION

PATENT NO. : 5,393,513

DATED : February 28, 1995

INVENTOR(S) : Long, Jr.

It is certified that error appears in the above-identified patent and that said Letters Patent is hereby corrected as shown below:

Column 7, line 39, change "rams" to --rates--.

Column 7, line 42, after exhibits, change "substantial-particle" to --substantial particle--.

Column 7, line 47, change "monobrominated" to --mono-brominated--.

Column 8, line 15, change "monobrominated" to --mono-brominated--.

Column 8, line 44, after flow, change "rams" to --rates--.

Signed and Sealed this

Thirteenth Day of June, 1995

*Attest:*

BRUCE LEHMAN

*Attesting Officer*   *Commissioner of Patents and Trademarks*